United States Patent [19]

Newman et al.

[11] Patent Number: 5,955,582
[45] Date of Patent: Sep. 21, 1999

[54] ANTIBODY AGAINST A 3-AMINOPHENYLBORONIC-GLYCATED PROTEIN COMPLEX AND ITS USE IN AN IMMUNOASSAY

[75] Inventors: Karel Z. Newman, Eden Prairie; Bruce Odegaard, Crystal; Godwin Orji Ogbonna, Eden Prarie; Jane A. Schmidt, Saint Paul, all of Minn.

[73] Assignee: Beckman Coulter, Inc., Fullerton, Calif.

[21] Appl. No.: 08/938,367

[22] Filed: Sep. 26, 1997

[51] Int. Cl.$^6$ .......................... C07K 16/18; G01N 33/53; G01N 33/536; G01N 33/538
[52] U.S. Cl. ...................... 530/387.1; 530/387.9; 530/388.1; 530/388.25; 530/388.9; 530/389.1; 530/389.3; 530/389.8; 530/391.3; 435/325; 435/326; 435/331; 435/337; 435/345; 435/7.1; 435/7.95; 435/975; 436/518; 436/523; 436/524; 436/532; 436/66; 436/67
[58] Field of Search .............................. 530/387.1, 387.9, 530/388.1, 388.25, 388.9, 389.1, 389.3, 389.8, 391.3; 435/325, 326, 331, 337, 345, 7.1, 7.9–7.95, 975; 436/578, 523, 524, 532, 66, 67

*Primary Examiner*—Paula K. Hutzell
*Assistant Examiner*—Nancy A. Johnson
*Attorney, Agent, or Firm*—William H. May; Margaret A. Kivinski

[57] ABSTRACT

Methods of preparing a boronate-antigen complex for immunization of animals, a monoclonal antibody specific for the same, an immunoassay method for detection of the complex and a method of calculating the amount of a target glycated protein within the sample useful in the diagnostic monitoring of diabetes are disclosed. An immunoassay kit based on this reagent is also disclosed.

32 Claims, No Drawings

ANTIBODY AGAINST A 3-AMINOPHENYLBORONIC-GLYCATED PROTEIN COMPLEX AND ITS USE IN AN IMMUNOASSAY

BACKGROUND OF THE INVENTION

1. Field of the Invention

This invention relates to methods for developing and utilizing antibodies, and more specifically to methods for developing and using antibodies with preferential recognition of phenylboronic acid complexes of glycosylated proteins.

2. Background of the Invention

Stasis of circulating plasma glucose levels is principally attributed to hormonal regulation. In the normal individual, this balance is achieved through the regulation of the antagonistic activity of insulin and glucagon. The diabetic patient has diminished or absent production of insulin which results in excess levels of glucose within the circulation. Treatments with exogenous insulin therapy are intended to reinstate control against excessive plasma glucose levels. Diagnostic methods for monitoring the long-term stability of blood glucose levels are important in the clinical treatment and maintenance of diabetic patients.

A chemical property of glucose is that the molecule can exist as a pyranose ring or linearized aldehyde. The aldehyde form can form a Schiff base structure when combined with 1° amines such as those found on the amino acid lysine or amino acid residues at the N-terminal end of proteins. This intermediate structure may reversibly dissociate to free glucose and the protein, or a chemical rearrangement (known as an Amadori rearrangement) can take place resulting in a new stabile chemical structure.

The level of glycation of proteins represents the average of the rises and declines in concentration of blood glucose and the length of time in contact with said proteins. Many different proteins can react with glucose as described leading to a subpopulation of proteins defined by the level of glycation. Several proteins have proven to be useful as markers for monitoring this glycation reaction. The protein hemoglobin has been a particularly useful and well acted marker for monitoring the efficacy of long-term insulin therapy. This is because the long half-life of hemoglobin (which can be up to 120 days) permits the assessment of average blood glucose levels over extended periods of time. Normal patients have a glycated hemoglobin content of 4–7% of the total, whereas untreated diabetics have levels of 12–20%. Clinicians use glycated hemoglobin levels to monitor the maintenance of normal physiologic glucose levels over extended time intervals, and as a predictive aid for other advanced sequelae of a prolonged hyperglycemic condition.

Hemoglobin exists as a tetramer comprised of two a and two b subunits. The molecule can be glycated at the N-terminal valine residues resident in either of the subunits. Additionally, the molecule can be glycated at any of several lysine moieties resident with either subunit. The level of glycation at each amino acid residue, while relatively proportional, is not equivalent.

Glycated hemoglobin has been measured in several ways including electrophoresis, cation exchange chromatography, affinity chromatography and by immunoassay. Each method has its benefits and detracting points. Electrophoresis can allow ready separation of the modified protein by relative mobility in an electric field or to its isoelectric point, however, variant forms of hemoglobin (for example, HbS) can result in spurious migration relative to normal forms of the molecule. Cation exchange chromatography can also afford ready separation of the protein but is very sensitive to ionic strength, pH and other sample loading conditions, and is again affected by aberrant hemoglobin variants. Affinity chromatography by capture and elution of the glycated fraction on a phenylboronate column is not affected by variant forms of the protein and is as such the most widely accepted method. However, affinity chromatography as with electrophoretic and chromatographic procedures are relatively laborious, difficult to standardize and cumbersome to automate.

Immunoassay methods have received considerable interest because they are particularly amenable to automation. Several strategies for development of such assays have been described and are well known to those practiced in the science of diagnostic immunochemistry. One such example depends on the use of an antibody directed toward the glycated form of the N-terminal valine on the hemoglobin, β-chain. This determinant, designated $HbA_{1c}$, is the most prevalent glycation site on hemoglobin representing approximately 40–45% of the total glycated content of the molecule. Several representative patents cover the immunologic recognition of this determinant including U.S. Pat. No. 4,647,654, U.S. Pat. No. 4,727,036, U.S. Pat. No. 4,658,022, U.S. Pat. No. 4,247,533, U.S. Pat. No. 4,478,744, U.S. Pat. No. 4,970,171, U.S. Pat. No. 5,206,144 and EP 329994.

The method described in U.S. Pat. No. 4,647,654 relates to the preparation of a glycated immunogenic synthetic antigen by contacting a peptide fragment representing the N-terminal amino acid sequence of $HbA_{1c}$ with glucose over an extending time interval, isolating the glycated fraction, coupling the fraction onto a carrier protein for presentation to an animal host. U.S. Pat. No. 4,727,036 describes a method for using monoclonal antibodies raised with the aforementioned antigen in developing an immunoassay to measure $HbA_{1c}$. Documents U.S. Pat. No. 4,970,171 and U.S. Pat. No. 4,658,022 describe denaturants and methods of denaturing hemoglobin so as to expose the $HbA_{1c}$ epitope for recognition by the aforementioned antibody. U.S. Pat. No. 4,247,533 describes a radioimmunoassay for detection of $HbA_{1c}$. U.S. Pat. No. 4,478,744 describes a method for raising polyclonal antibodies to $HbA_{1c}$. U.S. Pat. No. 5,206,144 describes a method for determining $HbA_{1c}$ levels without the need for chemical denaturation. And EP 329994 describes a synthetic antigen for raising antibodies to $HbA_{1c}$ that depends on the use of very specific chemical linker strategies.

While the high level of specificity of antibodies to $HbA_{1c}$ is a strength in methods dependent upon the same, said specificity has also proven to be a weakness as well. In particular, most such antibodies described to date have been found to show bias toward the recognition of normal forms of $HbA_{1c}$ and to a lesser extent or not at all with the variant forms of the protein. This behavior would be undesirable since it would result in the underestimation of blood $HbA_{1c}$ levels.

Accordingly there is a need to develop a reagent which draws from the recognized advantages of the phenylboronate chemistry while providing the advantages of an immunochemical approach.

SUMMARY OF THE INVENTION

This invention describes the design of a novel immunogen to raise an antibody to the intermediate complex of aminophenyl-boronate, the development of a monoclonal antibody with preferential recognition of the same and the use of such an antibody in the development of an immunoassay for the quantitation of boronate-complexed glycated hemoglobin. The present invention discloses a method for developing and using an antibody capable of preferentially binding to the complex which forms between an organoboronate and a glycated protein wherein the sugar moiety has at least one cis-diol arrangement. Specific examples are given for a monoclonal antibody developed to recognize 3-aminophenylboronic acid complexed with $HbA_{1c}$, although the invention is by no means limited to the recognition of that structure.

In accordance with embodiments of the present invention, an immunogen was generally prepared by coupling 1-deoxyfructosyl-N-hemoglobin peptide fragment-Gly-Gly-Gly-Cys to BSA(deglycated) using SMCC, although other peptide sequences, linker sequences and carrier molecules could be employed. The derivitized BSA was then contacted with 25 mM 3-amino-phenylboronic acid in 50 mM ammonium acetate buffer, pH 8.5. This complex is then presented to mice as a water-in-oil emulsified adjuvant. Hybridomas derived from mice immunized with the above complex are screened for the differential recognition of glycated hemoglobin complexed with the boronate derivative from either glycated and non-glycated hemoglobin. One clone, designated 849-10A3C6, was identified which exhibited the required characteristic and is the subject of a deposit at, 10801 University Boulevard, Manassas, Va. 20110-2209, the American Type Culture Collection made under the 1949 Budapest Treaty on Patents and Trade and has been given ATCC Accession Number HB-12400.

An assay method in accordance with an embodiment of the present invention for the use of this antibody to determine the glycated hemoglobin content in a blood sample comprises:

a) causing lysis of erythrocytes in the blood sample under conditions which liberate and enhance the solvent accessibility of epitopes on hemoglobin;

b) contacting diluted sample with a hemoglobin-specific capture phase comprising a paramagnetic particle in a matrix containing a boronate;

c) separating the complex formed between the boronate and the glycated hemoglobin from the unbound boronate and incubating the boronate-hemoglobin complex with a labeled complex-specific antibody;

d) separating free from bound labeled antibody;

e) detecting the level of signal generated by the label;

f) determining the amount of complex present; and g) calculating the relative amount of hemoglobin A1c present.

An alternative embodiment of the present invention does not require the above separation steps, but instead may include directly contacting a labeled complex-specific antibody and competing boronate-hemoglobin complex with the reaction mixture.

Although the following detailed description describes the application of the present invention for quantifying glycated hemoglobin capable of complexing with 3-amino-phenylboronic acid and determining levels of $HbA_{1c}$ from the amount of complex bound, the basic approach can be applied toward the development of antibodies to any of a multitude of glycosylated antigens including, but not limited to, glycated serum albumin or transferrin as adjunct diabetes markers, specific agalactosyl immunoglobulin variants associated with arthritis and other autoimmune disease states and assessment of pathological protein glycation not related to the above conditions.

DETAILED DESCRIPTION OF THE INVENTION

The present invention is directed to methods for developing and utilizing antibodies with preferred specificity for phenylboronic acid complexes of glycosylated proteins, for example, glycosylated albumin, $A_{1c}$ hemoglobin and non-$A_{1c}$ glycosylated hemoglobin. The structure of said complexes mimic the chemical interaction of glycosylated proteins on a phenylboronate column. In the examples presented, a monoclonal antibody is identified with preferential recognition of 3-aminophenylboronate complexed to the stable Amadori-rearrangement product formed between glucose and valine as normally presented on the β-chain of hemoglobin.

As used herein, the term "preferred specificity" means that the antibodies bind the phenylboronic acid complexes of glycosylated proteins to a significantly greater extent than any other constituent of the sample. Cross-reactivity with non-organoboronate glycated proteins is relatively low. In preferred embodiments, the cross-reactivity of the present antibodies with glycated proteins not complexed to an organoboronate is preferably less than about 50 percent, or more preferably less than about 20 percent.

The antibodies of the present invention have preferred specificity for a complex of glycated protein and an organoboronate. The complex recognized by the antibodies of the present invention is preferably formed of a glycated blood protein, such as, hemoglobin, serum albumin or transferrin, although any glycated protein is contemplated in which the sugar moiety has at least one cis-diol arrangement. A particularly preferred embodiment provides an antibody that binds a complex of a site on hemoglobin allowing for estimating levels of the HbA1c marker. The preferred organoboronate is 3-aminophenylboronate.

The present invention further includes an antigen useful for generating the above-described antibodies. A preferred embodiment of the antigen comprises a complex of 3-aminophenylboronate and a glycated hemoglobin peptide. A particularly preferred embodiment incorporates a peptide fragment linked to an appropriate carrier molecule. The antigen of this embodiment has the formula:

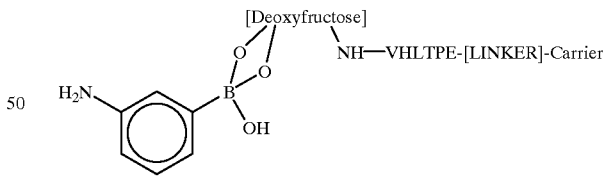

Any suitable carrier can be used to form the antigen. A preferred carrier is BSA.

The details related to the development and use of this invention are presented in the following series of non-limiting examples:

EXAMPLE 1

Antigen Preparation

The protected 1-deoxyfructosyl-N-Val was synthesized as the methyl ester by Ricerca, Inc. using the method of Xenakis et al (Synthesis, 541–543 (1983)), and the valine carboxylic acid was deprotected immediately before addition to the peptide. The terminal 1-deoxyfructosyl-N-Val derivative was added to the peptide as the Di-O-isopropylidene protected derivative. The complete peptide fragment, 1-deoxy-fructosyl-N-Val-His-Leu-Thr-Pro-Glu-Gly-Gly-Gly-Tyr-Cys, was synthesized by Anaspec, Inc. using Fmoc chemistry. The peptide Val-His-Leu-Thr-Pro-Glu-Gly-Gly-Gly-Tyr-Cys is identified as SEQ ID No:1. This peptide was coupled to bovine serum albumin which had been stripped of glycated fractions using an aminophenylboronate column. The peptide was coupled to the BSA using SPDP.

EXAMPLE 2

SPDP Linkage of the Peptide to Deglycated BSA

Pyridyl disulfide groups were introduced into deglycated bovine serum albumin by reaction with a 85-fold molar excess of sulfosuccinimidyl N-succinidyl-3-(2-pyridyldithio)-proprionate (SPDP in 100 mM sodium phosphate, 100 mM sodium chloride, pH 7.5; excess reagent was removed by gel filtration on a PD10 column (Pharmacia) in the same buffer. Conjugation was achieved by incubating modified BSA with the reduced peptide at a 22:1 molar ratio of carrier to peptide for one hour at room temperature. The conjugate was purified by size exclusion chromatography on PD10 column against 50 mM sodium phosphate, 100 mM NaCl, pH 7.0. The conjugate contained an estimated 17 incorporated peptide residues per BSA and bound quantitatively to a boronate affinity column.

EXAMPLE 3

Immunization

The glyco-peptide-BSA conjugate was diluted into 50 mM ammonium acetate, pH 8.5 with 25 mM 3-aminophenylboronic acid (Aldrich Chemical). The peptide was emulsified in Freund's adjuvant for injection into female Balb/C ByJ mice. Individual mice received 25 mg of antigen in complete Freund's adjuvant for the first two injections. Thereafter, mice received 25 mg injections of the antigen emulsified in incomplete Freund's adjuvant. Antibody titers to hemoglobin complexed with the organoboronate were monitored by the method described elsewhere.

EXAMPLE 4

Hybridoma Development

2–5 days prior to fusion, an immune animal(s) was given a single intravenous booster injection of 3-aminophenylboronate complexed to glyco-peptide-BSA conjugate. Individual animals described in Example 3 which exhibited elevated titers of antibody to the organoboronate complex of glycated hemoglobin relative to glycated hemoglobin alone were sacrificed by cervical dislocation.. The splenocytes were aseptically harvested. Cell fusion with a suitable plasmacytoma line was executed by a suitable method. Following plating and several days growth in culture, the cell supernatants were screened. Briefly, the screening medium was a suitable assay vessel (for example, a 96 well plate) sensitized with glycated hemoglobin. Half the plates were complexed with 25 mM 3-aminophenylboronate in 50 mM ammonium acetate, pH 8.5 and the other half were incubated with 50 mM ammonium acetate, pH 8.5, only. Duplicate samples of culture supernatant were then applied to both sets of plates. The vessels were then suitably developed to assess relative antibody binding. Wells showing antibody differential binding were retained for use in preparation of conjugates or solid phase.

EXAMPLE 5

Development of the Hybridoma 849-10A3C6.

Eight week old female Balb/C mice were immunized on a biweekly basis with 25 ug/dose of 3-aminophenylboronate complexed to glyco-peptide-BSA conjugate in Incomplete Freund's adjuvant by the intraperitoneal route. Three (3) days prior to fusion, mice were sacrificed by cervical dislocation, and the spleen surgically removed. The spleen was transferred to a petri dish containing 20 ml of Dulbecco's modified medium (DME) containing 100 ug/ml gentamycin. The splenocytes were freed by teasing the tissue apart. The splenocytes were washed once with DME, and combined in a 5:1 ratio with washed SP2/O cells. The cells were pelleted, excess supernatant removed, and the cells resuspended in 0.3 ml of buffered 50% polyethylene glycol solution (Boehringer). The cells are incubated at room temperature for 30 seconds prior to centrifugation at approximately 400×g for 6 minutes. Fused cells are then centrifuged, gently rinsed with DME, resuspended in Iscove's Modified DME with SP2/O conditioned medium and gently transferred to 100 mm petri dish. Following an overnight incubation at 37° C., the cells are diluted to $2 \times 10^6$ cells/ml in conditioned medium, and seeded into 96 well plates (150 ul/well). After 7–10 days, the supernatants are screened. Briefly, the screening medium was a Immulon I (Dynatech) 96 well plate sensitized with glycated hemoglobin. Half the plates were complexed with of 25 mM 3-aminophenylboronate in 50 mM ammonium acetate, pH 8.5 and the other half were incubated with 50 mM ammonium acetate, pH 8.5, only. Duplicate samples of culture supernatant were then applied to both sets of plates. The vessels were then suitably developed to assess relative antibody binding. Wells showing antibody differential binding were retained for use in preparation of conjugates or solid phase.

A few wells were identified which showed differential reactivity depending on the presence or absence of 3-aminophenylboronate. Within the one fusion, a hybridoma designated 849-10A3C6 was identified which distinguished between the presence and absence of 3-aminophenylboronate. The cell designated 849-8A10A3 was derived from that original colony.

EXAMPLE 6

Preparation of an Enzyme Conjugate of 849-10A3C6.

Maleimide groups were introduced into alkaline phosphatase by reaction with a 30-fold molar excess of sulfosuccinimidyl 4-(N-maleimidomethyl) cyclohexane-1-carboxylate in 0.2 M imidazole, pH 9.0; excess reagent was removed by gel filtration on a 1×28 cm column of Sephadex G50 in PBS. Thiol-groups were introduced into the antibody with 40 mM N-acetyl homocysteine thiolactone in 0.1 M sodium bicarbonate, 0.15 M NaCl, 1 mM EDTA, pH 8.0; excess reagent was removed on a second gel filtration column in the PBS+EDTA. Conjugation was achieved by incubating modified enzyme with modified antibody at a 2:1 molar ratio of ALP to antibody for two hours at room temperature. The conjugate was purified by size exclusion chromatography on Sephacryl S300 (1.5×120 cm) in Tris-buffered saline, pH 8.0.

EXAMPLE 7

Characterization of the Binding Properties of Antibody Produced by the Clone Designated 849-10A3C6.

Total human hemoglobin (approx. 5–7% glycated) was denatured for approximately 15 seconds by 10-fold dilution into 3 M guanidinium HCl in 50 mM Tris, pH 8.5. In turn, the sample was then diluted into 50 mM Tris buffered saline, pH 8.0 and contacted for 10 minutes with 20 mg paramagnetic particles sensitized with rabbit anti-human hemoglobin b-chain at 10 ug/mg particles. These particles were then rinsed to remove unbound hemoglobin and then contacted with 250 mM ammonium acetate, pH 8.0 with and without 25 mM 3-aminophenylboronic acid (Aldrich Chemical). After 5 minutes, the particles were separated and rinsed once with 250 mM ammonium acetate, pH 8.0. 20 ml of the antibody conjugate of Example 6 was added to the retained particles at 250 ng/ml and incubated for 10 minutes at room temperature. Afterward, the particles were washed extensively with 25 mM Tris, 100 mg/l FC-100, pH 8.0. Signal was generated with Lumiphos-530 (Lumigen) and detected on a Berthold luminometer. The monoclonal antibody conjugate exhibited a significant preferential binding activity for the hemoglobin treated with 3-aminophenylboronic acid.

The foregoing description of the invention and the examples demonstrating the application of the invention are but exemplary of the ways the invention can be utilized. That other variations will be useful will be apparent to those skilled in the art. Therefore, the present invention is to be considered limited only by the appended claims.

What is claimed:

1. An antibody which binds a complex of an organoboronate and a glycated protein, wherein said antibody binds the complex to a greater extent than non-organoboronate glycated proteins.

2. The antibody of claim 1 wherein the organoboronate is 3-aminophenylboronate.

3. The antibody of claim 1 wherein the glycated protein is a glycated blood protein.

4. The antibody of claim 3 wherein the glycated blood protein is selected from the group consisting of hemoglobin, serum albumin and transferrin.

5. The antibody of claim 4 wherein the glycated blood protein is hemoglobin.

6. The antibody of claim 5 wherein the hemoglobin is $HbA_{1c}$.

7. The antibody of claim 1 which is a monoclonal antibody.

8. The monoclonal antibody of claim 7 which corresponds to ATCC Accession Number HB-12400.

9. An immunoassay for detecting the presence or amount of a glycated protein in a test sample, the steps of said immunoassay comprising:

a) forming a complex between glycated protein in the test sample and an organoboronate;

b) contacting the sample with an antibody that binds the complex of the organoboronate and glycated protein, wherein the antibody binds the complex to a greater extent than non-organoboronate glycated proteins;

c) determining the amount of complex in the sample bound to antibody; and d) calculating an amount of the glycated protein species of interest from the amount of complex detected.

10. The immunoassay of claim 9, wherein in step a), the glycated protein is bound to a capture phase.

11. The immunoassay of claim 10, wherein the capture phase comprises an antibody specific for the glycated protein.

12. The immunoassay of claim 11, wherein the antibody specific for the glycated protein is coupled to a paramagnetic particle.

13. The immunoassay of claim 9, wherein, prior to step c), the antibody bound to the complex in the sample is separated from antibody which is unbound.

14. The immunoassay of claim 9, wherein the antibody is labeled.

15. The immunoassay of claim 13 wherein the label is an enzyme.

16. The immunoassay of claim 14 wherein the enzyme is alkaline phosphatase.

17. The immunoassay of claim 9, wherein an amount of complex of organoboronate and glycated protein is added to the test sample which competitively binds the antibody to the complex added to the test sample.

18. The immunoassay of claim 9, wherein the glycated protein is a glycated blood protein selected from the group consisting of hemoglobin, serum albumin and transferrin.

19. The immunoassay of claim 18, wherein the glycated blood protein is glycated hemoglobin.

20. The immunoassay of claim 19, wherein the glycated hemoglobin is $HbA_{1c}$.

21. A method for aiding in the diagnosis or treatment of diabetes comprising:

a) treating a sample from a patient with an organoboronate so as to form a complex between the organoboronate and glycated hemoglobin in the sample;

b) contacting the treated sample with an antibody specific for the complex;

c) detecting the presence or amount of antibody bound to the complex; and d) relating the presence or amount of the complex in the sample to a diabetic condition.

22. An immunoassay kit comprising a first antibody which binds a complex of an organoboronate and a glycated protein, said first antibody being coupled to an enzyme, and a second antibody which binds a complex of an organoboronate and a glycated protein.

23. The immunoassay kit of claim 22 further comprising a sample diluent.

24. The immunoassay kit of claim 23 further comprising a wash buffer.

25. The immunoassay kit of claim 24 further comprising a set of calibrators.

26. The immunoassay kit of claim 25 further comprising a reaction vessel.

27. An immunoassay kit comprising a first antibody which binds hemoglobin b-chain, and a second antibody which binds a complex of an organoboronate and a glycated peptide, wherein at least one of said antibodies is coupled to an enzyme.

28. The immunoassay kit of claim 27 further comprising a solid phase to which one of said antibodies is bound.

29. The immunoassay kit of claim 28 further comprising a sample diluent.

30. The immunoassay kit of claim 29 further comprising a wash buffer.

31. The immunoassay kit of claim 30 further comprising a set of calibrators.

32. The immunoassay kit of claim 31 further comprising a reaction vessel.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 11 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Val His Leu Thr Pro Glu Gly Gly Gly Tyr Cys
1             5                   10